July 25, 1944. G. SPARRE Plant Pat. 634
CHRYSANTHEMUM PLANT
Filed Jan. 12, 1944
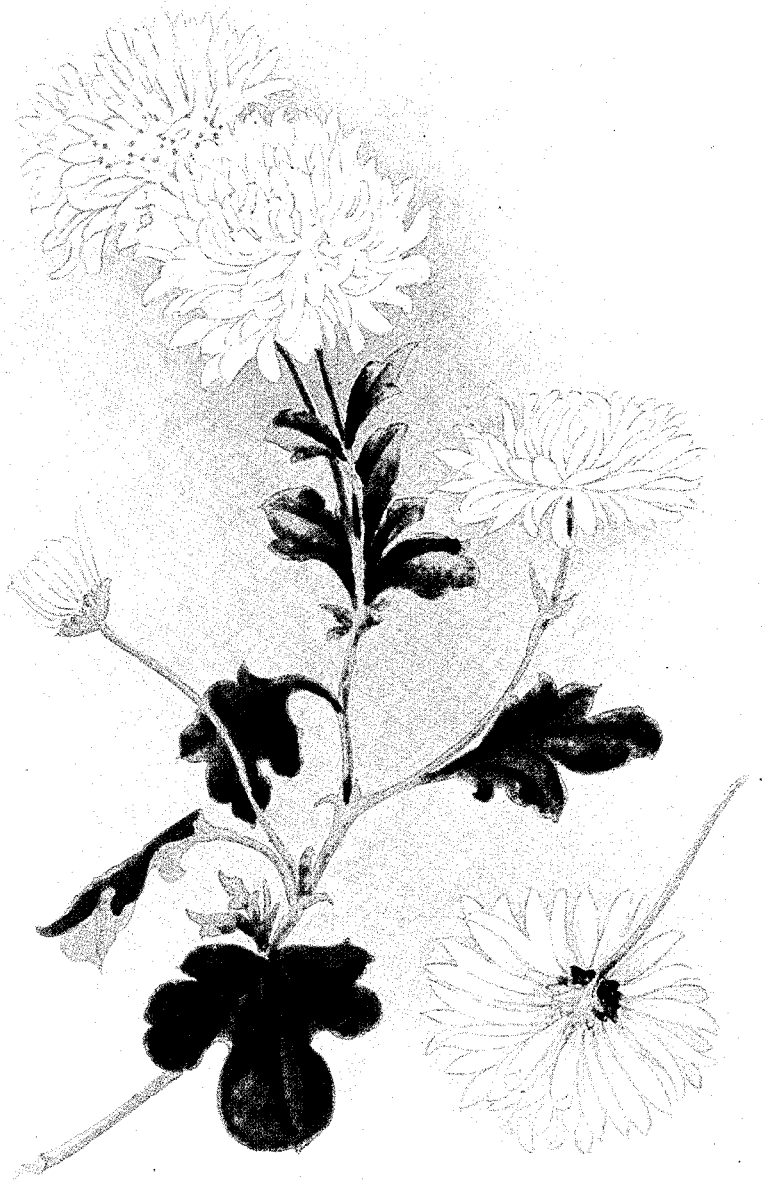
WITNESS
Addison F. Avery
INVENTOR
GUSTAV SPARRE
BY John H. Leonard
HIS ATTORNEY Patented July 25, 1944

Plant Pat. 634

UNITED STATES PATENT OFFICE

634

CHRYSANTHEMUM PLANT

Gustav Sparre, Clarkson, Ontario, Canada, assignor to The Wayside Gardens Company, Mentor, Ohio, a corporation of Ohio Application January 12, 1944, Serial No. 517,951

1 Claim. (Cl. 47—60)

This invention relates to a new and distinct variety of chrysanthemum indicum.

The new variety was produced by me by crossing the chrysanthemum indicum known as Early Yellow, as the seed parent, with the chrysanthemum indicum known as Alice Cummings, as the pollen parent.

The new variety was first produced by me in 1937 at The Sheridan Nurseries, Ltd., Clarkson, Ontario, Canada. It was subsequently asexually reproduced by me first in 1938 at which time several plants were asexually reproduced by root cuttings of the original. Subsequently, other plants were asexually reproduced from root cuttings of the original plant and of the first said reproductions and grown for test purposes in the fields of The Wayside Gardens Company, Mentor, Ohio. All of the asexually reproduced plants were true to the original.

The plant has openly branched roots which are of average size for this type of plant and shallow rooted, the lateral spread of the roots being about the same as the upper spread of the plant itself. The resistance of the roots and the plant generally to diseases and drought is excellent, as also is the winter resistance, having survived 28° below zero (F.) at Clarkson, Ontario. The plant thrives in any good garden soil under growing conditions suitable for chrysanthemums.

The exposed plant is herbaceous, generally globular and bushy. The plant grows to a height of from eighteen to twenty-four inches with a spread of from eighteen to twenty inches. The growth is medium and the exposed plant structure is exceedingly resistant to disease and drought. The plant prefers full sun, preferably clay loam or sandy loam, well drained.

The plant has stiff, much branched stalks which are adequate to support the bloom well and are brittle. Generally, the stalks are uniformly colored a dark green, comparable to Maerz and Paul Plate No. 23-J-5 to 8 and this color applies generally to old and new growth. The stalks measure from twelve to fifteen inches high and are smooth in texture. The manner of growth from the roots is generally single the first year and grouped in succeeding years, with opposite branches.

The foliage is comparatively dense, the leaves generally being arranged alternately. They are abundant in quantity. The leaves, both old and new, are a dull green on the upper surface comparable to Maerz and Paul Plate No. 24-E-6. On the under surface they are a somewhat lighter green. The color is generally uniform for all leaves. The size of the leaf is average for a chrysanthemum indicum and smooth and glossy on the upper face and dull on the lower face. Their persistence on the plant is excellent. The leaves are unusual in that they have a pronounced glossy appearance and are not serrated to the same extent as those of most chrysanthemums.

For both growth and flowering, the plants prefer full sun or partial shade with a southern exposure but do well under the usual sun and shade conditions in which other varieties of chrysanthemums grow effectively.

The blooming period extends from September or earlier to heavy frosts in the late fall. The plant blooms continuously for periods of six weeks or over. The buds are small and globular. They are borne upright and singly. When the sepals first divide and the petals begin to open the general tone of the buds is golden yellow to orange, comparable to Maerz and Paul Plate No. 10-L-7 to 10.

The pedicels are relatively short. The flower heads are from two to two and one half inches in diameter and average fifty to seventy-five blooms to the individual plant. Each flower averages from two hundred to three hundred petals. At the outer edges of the petals (top face) the color, starting from a light golden yellow, Maerz and Paul Plate 10-L-5 to 10-L-7, shades into the center of the petal down to a rich orange yellow, Maerz and Paul Plate 10-L-9, and shading farther toward the bases of the petals near the center of the flower to a near chrome orange comparable to Maerz and Paul Plate No. 10-L-12. The reverse of the petals is a pale or light chrome yellow comparable to Maerz and Paul Plate 10-L-4. The general tonality from a distance is a light golden yellow comparable to Maerz and Paul Plate Nos. 10-L-5 to 8. There is little discoloration and the general tonatility remains the same in favorably cool weather, the color being best in cool weather and less sunshine. The petals in form are comparatively thin, narrow, boat-shaped and of smooth texture, forming a dense cluster but not imbricated. The flower is generally round and cushion-like.

The persistence of the cut and uncut flowers is good and of average lasting quality both cut and uncut. The stamens are composite but not unusual, of pale yellow and about fifteen to twenty to each flower. The fruit is insignificant and sparse.

The unusual characteristics of the plant are its exceeding vigor and ability to withstand severe winters in the North Temperate Zone, whether protected or unprotected, its early and continuous blooming, its exceptional resistance to disease and good resistance to drought, and the exceptional solidarity or compactness of petals of the flower heads.

Each of the characteristics of the plant mentioned in the next preceding paragraph and the combinations of part or all thereof, I claim distinguish the new variety from all other known varieties of chrysanthemum indicum.

I claim:

The new variety of chrysanthemum indicum herein shown and described characterized in the outstanding and exceptional resistance to cold, drought and disease, the unusually compact and solid head of the flower, the early and continuous blooming habit of the plant and hardiness above average.

GUSTAV SPARRE.